(12) United States Patent
Wack et al.

(10) Patent No.: US 7,463,369 B2
(45) Date of Patent: Dec. 9, 2008

(54) SYSTEMS AND METHODS FOR MEASURING ONE OR MORE CHARACTERISTICS OF PATTERNED FEATURES ON A SPECIMEN

(75) Inventors: Dan Wack, Los Altos, CA (US);
Haiming Wang, Fremont, CA (US);
Kenneth P. Gross, San Carlos, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 337 days.

(21) Appl. No.: 11/277,856

(22) Filed: Mar. 29, 2006

(65) Prior Publication Data

US 2007/0229852 A1    Oct. 4, 2007

(51) Int. Cl.
*G01B 11/14* (2006.01)
*G01N 21/55* (2006.01)

(52) U.S. Cl. .................. 356/625; 356/601; 356/445; 356/364; 356/369

(58) Field of Classification Search ......... 356/630–632, 356/364–369, 445, 448; 250/225, 559.19, 250/559.27
See application file for complete search history.

(56) References Cited

U.S. PATENT DOCUMENTS

| | | | |
|---|---|---|---|
| 5,166,752 A | | 11/1992 | Spanier et al. |
| 5,432,607 A | * | 7/1995 | Taubenblatt ................ 356/364 |
| 5,596,406 A | | 1/1997 | Rosencwaig et al. |
| 5,596,411 A | * | 1/1997 | Fanton et al. ............... 356/369 |
| 5,703,686 A | | 12/1997 | Leroux |
| 5,880,845 A | | 3/1999 | Leroux |
| 5,889,593 A | | 3/1999 | Bareket |
| 5,986,762 A | * | 11/1999 | Challener .................... 356/614 |
| 6,134,012 A | * | 10/2000 | Aspnes et al. ............... 356/369 |
| 6,297,880 B1 | * | 10/2001 | Rosencwaig et al. ........ 356/369 |
| 6,556,284 B1 | | 4/2003 | Leroux |
| 6,597,006 B1 | * | 7/2003 | McCord et al. ......... 250/559.19 |
| 6,654,131 B2 | | 11/2003 | Opsal et al. |
| 6,678,046 B2 | * | 1/2004 | Opsal .......................... 356/369 |
| 6,819,426 B2 | * | 11/2004 | Sezginer et al. ............. 356/401 |
| 7,046,376 B2 | * | 5/2006 | Sezginer ..................... 356/601 |
| 7,068,363 B2 | * | 6/2006 | Bevis et al. ............... 356/237.5 |
| 7,224,471 B2 | * | 5/2007 | Bischoff et al. ............. 356/601 |
| 2004/0196460 A1 | | 10/2004 | Dobschal et al. |

OTHER PUBLICATIONS

Byrne et al., "Angular scanning mechanism for ellipsometers," Technical Notes, Applied Optics, vol. 30, No. 31, Nov. 1991, pp. 4471-4473.

(Continued)

*Primary Examiner*—Sang Nguyen
(74) *Attorney, Agent, or Firm*—Baker & McKenzie LLP

(57) ABSTRACT

Systems and methods for measuring one or more characteristics of patterned features on a specimen are provided. One system includes an optical subsystem configured to acquire measurements of light scattered from the patterned features on the specimen at multiple angles of incidence, multiple azimuthal angles, and multiple wavelengths simultaneously. The system also includes a processor configured to determine the one or more characteristics of the patterned features from the measurements. One method includes acquiring measurements of light scattered from the patterned features on the specimen at multiple angles of incidence, multiple azimuthal angles, and multiple wavelengths simultaneously. The method also includes determining the one or more characteristics of the patterned features from the measurements.

20 Claims, 7 Drawing Sheets

OTHER PUBLICATIONS

Petit et al., "A new analysis strategy for CD metrology using rapid photo goniometry method," Proceedings of SPIE vol. 5375, 2004, pp. 210-221.

Genet et al., "Depolarization induced by subwavelength metal hole arrays," arXiv:physics/0311137 v1, Nov. 2003, pp. 1-4.

Jun et al., "Simulation of depolarization effect by a rough surface for spectroscopic ellipsometry," J. Opt. Soc. Am. A, vol. 20, No. 6, Jun. 2003, pp. 1060-1066.

Barnes et al., "Photonic surfaces for surface-plasmon polaritons," J. Opt. Soc. Am. A, vol. 14, No. 7, Jul. 1997, pp. 1654-1661.

Kitson et al., "Surface profile dependence of surface plasmon band gaps on metallic gratings," J. Appl. Phys., vol. 79, No. 9, May 1996, pp. 7383-7385.

Watts et al., "The influence of grating profile on surface plasmon polariton resonances recorded in different diffracted orders," Journal of Modern Optics, vol. 46, No. 15, 1999, pp. 2157-2186.

Pipino et al., "Surface-profile dependence of photon-plasmon-polariton coupling at a corrugated silver surface," J. Opt. Soc. Am. B, vol. 11, No. 10, Oct. 1994, pp. 2036-2045.

Watts et al., "Polarization conversion from blazed diffraction gratings," Journal of Modern Optics, vol. 44, No. 6, 1997, pp. 1231-1241.

Coulombe et al., "Modal characteristics of short-pitch photoresist gratings exhibiting zero-order diffraction anomalies," J. Opt. Soc. Am. A, vol. 16, No. 12, Dec. 1999, pp. 2904-2913.

* cited by examiner

SYSTEMS AND METHODS FOR MEASURING ONE OR MORE CHARACTERISTICS OF PATTERNED FEATURES ON A SPECIMEN

BACKGROUND OF THE INVENTION

1. Field of the Invention

The present invention generally relates to systems and methods for measuring one or more characteristics of patterned features on a specimen. Certain embodiments relate to a system that includes an optical subsystem configured to acquire measurements of light scattered from patterned features on a specimen at multiple angles of incidence, multiple azimuthal angles, and multiple wavelengths simultaneously.

2. Description of the Related Art

The following description and examples are not admitted to be prior art by virtue of their inclusion in this section.

Metrology processes are used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined from currently used inspection tools. For example, metrology processes are used to measure one or more characteristics of a wafer such as a dimension (e.g., line width, thickness, etc.) of patterned features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

Generally, the sensitivity of scatterometric metrology systems to certain variables of the specimen under test is closely related to the angle of incidence (AOI, which will be represented by the symbol $\theta$ in following description) and azimuthal angle (represented by the symbol $\phi$) of the beam falling onto the specimen. One typical example of a metrology system measurement is the measurement of the thickness of a thin silicon oxide ($SiO_2$, which is commonly referred to as "oxide") film on a silicon substrate. The sensitivity of the measurement to the oxide thickness is maximized when the AOI is set close to the Brewster angle of the silicon substrate. This AOI leads to the design of spectroscopic ellipsometers (SE) with an AOI at approximately 71 degrees, which has been an optimized system setup for most film measurement applications. In addition, because most materials in semiconductor manufacturing are optically isotropic, azimuthal angle is largely ignored in film thickness measurements. For critical dimension (CD) measurements, however, the above AOI is not necessarily the best configuration as far as the sensitivity to certain CD characteristics is concerned.

There are some ways for varying the AOI in spectroscopic systems. Nevertheless, none of them has been applied for CD measurements. The simplest and most straight-forward way for varying AOI in spectroscopic systems is to change both the direction of the incident beam and the collection beam simultaneously. Tools having such capability include the VASE® (Variable Angle Spectroscopic Ellipsometry) series of systems that are commercially available from J. A. Woollam Co., Inc., Lincoln, Nebr. A modified version of this "2-θ" scanning scheme is described in D. M. Byrne and D. L. MacFarlane, "Angular scanning mechanism for ellipsometers," *Applied Optics*, 30(31), 4471-4473, (1991), which is incorporated by reference as if fully set forth herein, in which two flat turning mirrors are used to change the angle of the incident beam and the reflection beam simultaneously.

The most significant drawback of this scheme, particularly for CD measurements, is the requirement of two synchronized rotations. As the technology node continuously decreases to 45 nm and lower, the performance requirements for metrology systems are continuously raised. To meet leading-edge specifications of precision, accuracy, and tool-to-tool matching for CD measurements, it is critical to calibrate system parameters substantially accurately and to maintain a relatively high level of stability in these parameters during measurements. AOI is one of these critical system parameters that needs to be exactly calibrated and stabilized. The AOI of the above VASE design, as a result of two rotating elements, is difficult to calibrate and maintain. This difficulty is a major hurdle preventing the above VASE design from being adopted in semiconductor production lines, and as a result, the main applications of systems based on this scheme are mostly research applications. In addition, this scheme does not have the capability to vary azimuthal angles.

One attempt to acquire AOI- and azimuthal angle-resolved information simultaneously has been developed by various companies, which involves using a focusing mirror or lens with a relatively large numerical aperture (NA). U.S. Pat. No. 5,889,593 to Bareket, which is incorporated by reference as if fully set forth herein, illustrates the basic principle of this scheme for reflectometry instead of ellipsometry. In this type of scheme, a relatively large NA objective (e.g., an objective having an NA of at least 0.5, and preferably up to 0.95), either a mirror or lens (such as a microscope objective), focuses an illumination beam onto the specimen. Because of the large NA, the incident beam includes many different AOIs (in the case of an NA of 0.95, AOIs ranging from 0° to 70°). To resolve the AOIs, an imaging array is used as a light detector. Signals corresponding to different AOIs and azimuthal angles fall onto different pixels of the imaging array and are recorded. Similar schemes are also disclosed in U.S. Pat. Nos. 5,596,406 to Rosencwaig et al., 5,703,686 to Leroux, 5,880, 845 to Leroux, 6,556,284 to Leroux, and 6,654,131 to Opsal et al., as well J. Petit, et al., "A new analysis strategy for CD metrology using rapid photo goniometry method," *Proceedings of SPIE* 5375, 210 (2004), all of which are incorporated by reference as if fully set forth herein.

One major disadvantage of this type of angle-resolved design is the difficulty to perform spectroscopic measurements as well, which involves a three-dimensional data cube of AOI, azimuthal angle, and wavelength. Recording this data simultaneously is beyond the capability of a two-dimensional imaging array. To resolve the angular and spectral information, some complex wavelength multiplexing-demultiplexing is needed, which may either not work efficiently or may increase the complexity and reduce the reliability of the system.

For example, in a monochromatic measurement system, the system configuration is relatively simple and straightforward. If AOI-resolved measurements are desired, a linear imaging array can be placed in the direction parallel to the plane of incidence. In this manner, signals corresponding to different AOIs are mapped to different pixels in the imaging array. If azimuthal angle-resolved measurements are desired, an arc-shaped mask can be placed in the plane of an exit aperture to just pick up reflection signals with a given AOI but various azimuthal angles as described by J. Petit, et al. in the article incorporated by reference above. In this type of azimuthal angle-resolved system, a two-dimensional detector array is used even though only a few pixels in the two-dimensional array corresponding to the arc-shaped mask are used for the measurements.

However, when spectroscopic measurements are desired, some complex means is needed to resolve the spectral information. One method for resolving the spectral information is to record signals of different wavelengths at different times such as by using a monochromator or filter wheel to allow light of only one wavelength to enter the system at a time. The obvious drawback of this method is that the throughput of the measurement system is reduced, and as the number of wavelengths at which measurements are performed increases, the throughput of the system decreases.

In the above disclosed methods, the chief rays of illumination and reflection are at normal incidence. As such, the largest AOI is limited by the NA of the focusing optics. As a consequence, careful correction of the aberrations of the focusing optical systems are needed. In addition, because of the large NA, the illumination spot is relatively small, typically in the range of a few µm. However, scatterometry is based on model-based analysis, which in general is performed utilizing rigorous coupled-wave analysis (RCWA), in which illumination of a periodic patterned structure is required. According to the International Technology Roadmap for Semiconductors (ITRS), the most challenging layers have relatively small CDs with relatively large pitches (e.g., typically CDs of less than 50 nm and pitches in the range of 800 nm). When the illumination spot is too small, the periodicity of the patterned features under measurement may not hold anymore.

U.S. Pat. No. 5,166,752 to Spainer et al. and U.S. Patent Application Publication No. 2004/0196460 A1 by Dobschal et al., which are incorporated by reference as if fully set forth herein, disclose systems that are configured to direct light to a specimen at an oblique AOI. Additionally, these two systems include a two-dimensional detector in combination with a dispersion element (such as a grating or a prism) for AOI-resolved spectroscopic measurements. In such systems, columns of the detector correspond to signals with a fixed wavelength but various AOIs, and rows of the detector correspond to signals with a fixed AOI but various wavelengths. Therefore, a pixel in a specific row and column of the detector will theoretically pick up only the signal for a specific wavelength and a specific AOI.

A significant problem related to such a system configuration is shown in FIG. 1 of U.S. Pat. Nos. 5,596,406 to Rosencwaig et al. and 6,654,131 to Opsal et al., which are incorporated by reference above, and described in the corresponding description of this figure. Briefly, because of the finite sizes of the illumination and reflection beams, a pixel in a specific row and column of the detector will not only record the signal corresponding to the wavelength and AOI specified by the column number and row number. Instead, signals from adjacent pixels corresponding to different wavelengths and AOIs may also fall onto this pixel thereby degrading both the spectral and angular resolutions.

To overcome the above problem, Rosencwaig et al. and Opsal et al. suggest using a rectangular aperture that is elongated in one direction and placed in front of the dispersion element. In this manner, only signals corresponding to the azimuthal angle parallel to the long-direction of the aperture can be picked up thereby reducing the three-dimensional data cube (AOI, azimuthal angle, wavelength) into a two-dimensional "data plane" (AOI, wavelength). As a result, this system configuration effectively eliminates the resolution degradation problem in the systems disclosed by Spainer et al. Nevertheless, this configuration creates its own problem, namely, that the light power utilization is much lower because only a relatively small portion of the light corresponding to a given azimuthal angle is collected.

Furthermore, it is more difficult to facilitate azimuthal angle-resolved spectroscopic measurements than the AOI-resolved spectroscopic measurements disclosed above, for two reasons. First, when the chief ray is at normal incidence, the exit aperture is mapped to an entire reflection light cone corresponding to azimuthal angles in the range of 0 degrees to 360 degrees. On the other hand, under oblique incidence, the range of azimuthal angles is significantly reduced, which is defined by the NA of the collection optics. However, for CD measurements, it may be desirable to perform measurements at azimuthal angles in a relatively large range, which may vary from 0 degrees to 90 degrees. Obviously, the systems disclosed by Spainer et al. and Dobschal et al. are insufficient for this purpose.

In addition, at both normal and oblique incidence, to perform azimuthal angle-resolved measurements, an arc in the exit aperture (such as that defined by an arc-shaped mask described in the paper by J. Petit et al.) has to be mapped to a line in the direction parallel to one of the axes in the two-dimensional detector array. Optically, such mapping is complex and expensive to implement.

Accordingly, it may be advantageous to develop systems and methods for measuring one or more characteristics of patterned features on a specimen that can acquire measurements of light scattered from the patterned features on the specimen at multiple AOIs, multiple azimuthal angles, and multiple wavelengths simultaneously while eliminating one or more of the disadvantages of the methods and systems described above.

SUMMARY OF THE INVENTION

The following description of various embodiments of systems and methods is not to be construed in any way as limiting the subject matter of the appended claims.

One embodiment relates to a system configured to measure one or more characteristics of patterned features on a specimen. The system includes an optical subsystem configured to acquire measurements of light scattered from the patterned features on the specimen at multiple angles of incidence (AOIs), multiple azimuthal angles, and multiple wavelengths simultaneously. The system also includes a processor configured to determine the one or more characteristics of the patterned features from the measurements.

In one embodiment, the one or more characteristics include critical dimension (CD) of the patterned features. In another embodiment, the multiple AOIs and the multiple azimuthal angles are selected such that the measurements of the light include measurements of surface plasmon waves and guided waves. In some embodiments, the measurements of the light include measurements of surface plasmon waves and guided waves, and the one or more characteristics include CD of the patterned features. In one such embodiment, the measurements are more sensitive to the CD than if the measurements do not include the measurements of the surface plasmon waves and the guided waves. In a further embodiment, the one or more characteristics include CD of the patterned features, and the multiple AOIs and the multiple azimuthal angles are selected such that the measurements are more sensitive to the CD than if the measurements were acquired at different AOIs and different azimuthal angles.

In one embodiment, the multiple AOIs are selected based on an optimal AOI and potential variations in the one or more characteristics. In such an embodiment, the multiple azimuthal angles may be selected based on an optimal azimuthal angle and the potential variations in the one or more characteristics. In another embodiment, the system includes a stage configured to support the specimen during acquisition of the measurements. In one such embodiment, the stage is configured to rotate the specimen such that the measurements can be acquired at the multiple azimuthal angles.

In some embodiments, the optical subsystem includes an exit aperture that is adjustable such that the measurements can be acquired at the multiple AOIs and the multiple azimuthal angles. In another embodiment, the optical subsystem includes an exit aperture, and the multiple AOIs and the multiple azimuthal angles are mapped across two dimensions of the exit aperture. In an additional embodiment, the optical subsystem includes a two-dimensional detector. In one such embodiment, the multiple wavelengths are mapped along a first dimension of the detector, and the multiple AOIs and the multiple azimuthal angles are mapped along a second dimension of the detector. In a further embodiment, the optical subsystem includes an exit aperture, a two-dimensional detector, and a set of optical fibers. In one such embodiment, the multiple AOIs and the multiple azimuthal angles are mapped across two dimensions of the exit aperture. The multiple AOIs and the multiple azimuthal angles are mapped along one dimension of the detector, and the set of optical fibers is configured to direct light from the two dimensions of the exit aperture to the one dimension of the detector.

In one embodiment, the optical subsystem includes a two-dimensional detector that is electronically adjustable such that the measurements can be acquired at the multiple AOIs and the multiple azimuthal angles. In another embodiment, the measurements at the multiple AOIs and the multiple azimuthal angles are averaged over a portion of the numerical aperture (NA) of the optical subsystem.

In one embodiment, the measurements of the light are responsive to surface plasmon induced depolarization of the light. In one such embodiment, the one or more characteristics include CD and profile of the patterned features, and the measurements are more sensitive to the CD and the profile than measurements that are not responsive to the surface plasmon induced depolarization. In another embodiment, the one or more characteristics include line edge roughness (LER) of the patterned features. In one such embodiment, the processor is configured to determine the LER by determining surface plasmon induced depolarization of the light and LER induced depolarization of the light using the measurements at the multiple AOIs and the multiple azimuthal angles.

In one embodiment, the measurements include ellipsometric measurements. In another embodiment, the measurements include reflectometric measurements. In some embodiments, the optical subsystem is configured to direct the chief ray of illumination to the specimen at an oblique AOI. In a further embodiment, the patterned features include isolated patterned features. Each of the embodiments of the system described above may be further configured as described herein.

Another embodiment relates to a method for measuring one or more characteristics of patterned features on a specimen. The method includes acquiring measurements of light scattered from the patterned features on the specimen at multiple AOIs, multiple azimuthal angles, and multiple wavelengths simultaneously. The method also includes determining the one or more characteristics of the patterned features from the measurements. The method may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
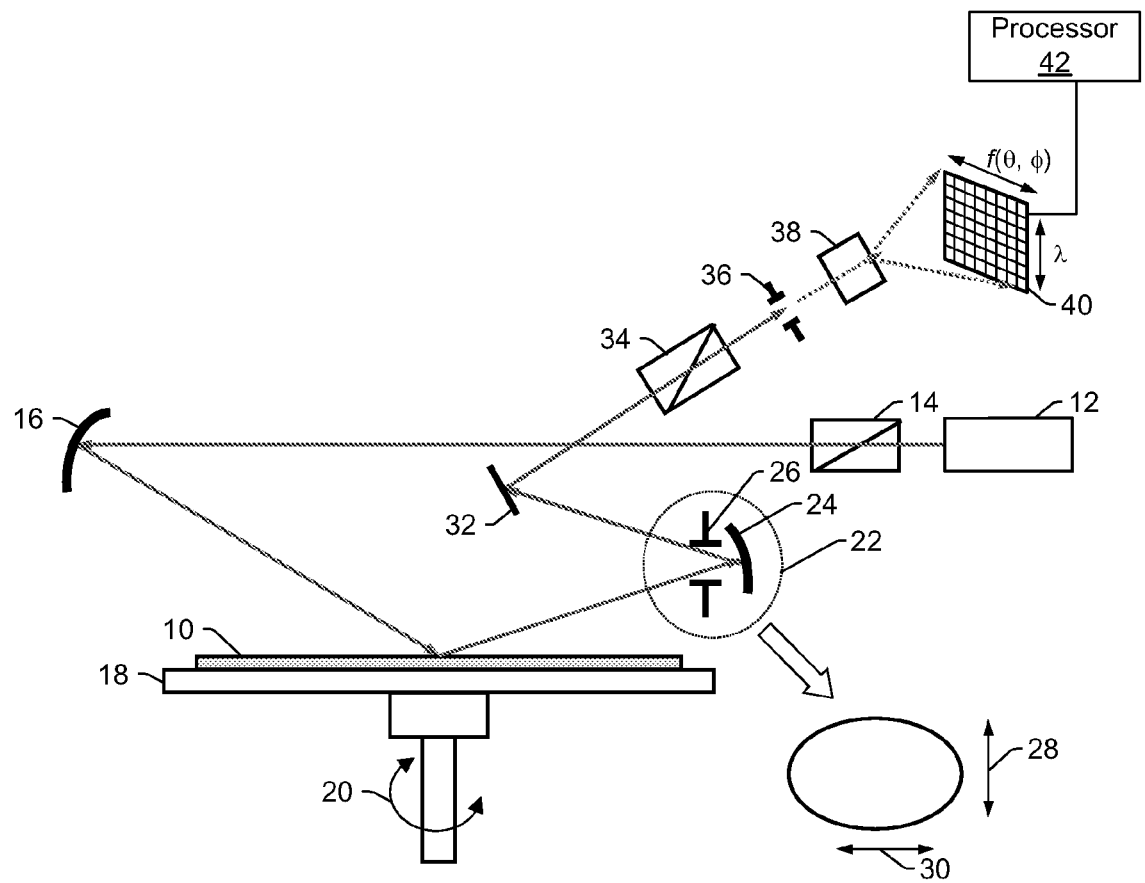
FIG. 1 is a schematic diagram illustrating a side view of one embodiment of a system configured to measure one or more characteristics of patterned features on a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, a conductive material, and a semiconductor layer (e.g., an epitaxial layer). Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

The embodiments described herein generally relate to systems and methods for enhancing the sensitivity of optical scatterometric systems (including, but not limited to, for example, spectroscopic reflectometry and spectroscopic ellipsometry (SE) systems) for measuring extremely challenging layers in the next lithography technology node. In particular, the method embodiments and the system (e.g., SE apparatus) embodiments described herein are capable of measuring spectral signals at variable angles of incidence (AOIs) and azimuthal angles, without the disadvantages of currently used methods and systems described in the references mentioned in the above section entitled "Description of the Related Art." In some embodiments described herein, an angle-resolved spectroscopic scatterometric system is configured to use surface plasmon waves and guided waves for enhancing the sensitivity of measurements of critical dimensions (CDs) and profiles of patterned feature.

According to the International Technology Roadmap for Semiconductors (ITRS), one of the most difficult challenges for metrology is to measure extremely isolated, relatively small lines or three-dimensional patterned features (or "patterned structures"). Typical such structures have CDs of less than 50 nm, with heights less than 100 nm, and pitches of about 800 nm. Conventional scatterometry based optical systems may not have sufficient sensitivity to measure characteristic(s) of these features. Excitation of surface plasmon waves (SPWs) and/or guided waves provides a promising solution for the above challenging layers.

Generally, the sensitivity of scatterometric systems to certain characteristics of the specimen under test is closely related to the AOI (which will be represented by the symbol $\theta$ in the following description) and azimuthal angle (represented by the symbol $\phi$) of the beam falling onto the specimen. One example of such a characteristic is the measurement of the thickness of a relatively thin silicon oxide film ($SiO_2$, which is commonly referred to as "oxide") on a silicon substrate. The sensitivity of measurements of the oxide thickness is maximized when the AOI is set close to the Brewster angle of the silicon substrate. This relationship between sensitivity and AOI leads to the design of SE systems with an AOI at approximately 71 degrees, which has been an optimized system setup for most film measurement applications. In addition, because most materials used in semiconductor manufacturing are optically isotropic, azimuthal angle is largely ignored in film thickness measurements.

In CD measurements, however, the AOI described above is not necessarily the best configuration for the system as far as the sensitivity to certain CD characteristics is concerned. In addition, more characteristics of the patterned features such as middle CD (MCD), grating/contact height (HT), side wall angle (SWA), and other profile characteristics may need to be measured.

Under certain conditions, it is possible to excite SPWs or guided waves (both of which will be referred to as "surface waves" in the following description, if it is not required to distinguish between them) in a specimen that includes either two-dimensional gratings or three-dimensional patterned features (such as contacts) on top of, or embedded in, a film stack with multiple layers. These excited surface waves, propagating in the direction parallel to the specimen surface, will enhance electromagnetic fields on certain parts of the patterned features thereby increasing the sensitivity of scatterometric signals to CD of the patterned features and certain profile characteristics of the patterned features. Using the excited surface waves for increasing the sensitivity of CD measurements is particularly powerful for challenging layers such as those described further above with patterned features having substantially small CDs and extremely isolated patterned features with substantially large pitches. Such enhancements may be particularly powerful at relatively large azimuthal angles (about 80 degrees), which makes azimuthal angle-resolved spectroscopic measurements particularly attractive.

To excite these surface waves at certain light wavelengths (a set of $\lambda$ values), both the AOI and the azimuthal angle of the measurement system may be adjusted or fine tuned. As a result, it is advantageous to develop measurement systems that can acquire information (a "scatterometric signature" or "signature") across a certain spectral range, a given AOI range, and a specific azimuthal angle range. In other words, it would be advantageous to develop a system that has the capability to acquire a "data cube" in the $\lambda$, $\theta$, $\phi$ space.

As a result, it is desirable to develop angle-resolved spectroscopic scatterometric systems with the capability to adjust both AOI and azimuthal angle in parallel. This capability will significantly enhance the sensitivity of the systems to CD and profile characteristics for various application layers, particularly for these challenging layers with extremely isolated small patterned features.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to measure one or more characteristics of patterned features on a specimen. The patterned features may include any of the patterned features described herein. For example, in one embodiment, the patterned features include isolated patterned features. The system includes an optical subsystem configured to acquire measurements of light scattered from the patterned features (not shown) on specimen 10 at multiple AOIs, multiple azimuthal angles, and multiple wavelengths simultaneously. The optical subsystem includes light source 12. Light source 12 may be a broadband light source. The broadband light source may include any appropriate broadband light source known in the art. In addition, the light source may include any other appropriate light source known in the art.

Light from light source 12 is directed to rotating polarizer 14, which may include any appropriate polarizing component known in the art. Light exiting rotating polarizer 14 is directed to focusing mirror 16. Focusing mirror 16 may include any appropriate focusing mirror known in the art. Focusing mirror 16 is configured to direct the light to specimen 10. In particular, focusing mirror 16 is configured to direct the light to specimen 10 at an oblique AOI. In one embodiment, therefore, the optical subsystem is configured to direct the chief ray of illumination to the specimen at an oblique AOI. In this manner, as shown in FIG. 1, the light from a light source (e.g., a broadband light source), after being polarized by rotating polarizer 14, is focused onto the specimen surface by focusing mirror 16.

In one embodiment, the system includes stage 18 that is configured to support specimen 10 during acquisition of the measurements. In some embodiments, stage 18 is configured to rotate the specimen (e.g., in directions illustrated by arrow 20) such that the measurements can be acquired at the multiple azimuthal angles. The stage may include any appropriate mechanical or robotic assembly known in the art.

The optical subsystem may also include adjustable collection mirror 22 that is configured to collect light scattered from patterned features on the specimen. Adjustable collection mirror 22 includes collection mirror 24 and exit aperture 26. Light scattered from the patterned features on the specimen is collected by collection mirror 24 in front of which is positioned exit aperture 26. Exit aperture 26 may be adjustable in two dimensions 28 and 30 to alter the multiple AOIs and multiple azimuthal angles of the light scattered from the patterned features on the specimen that are collected by collection mirror 22. In one embodiment, therefore, the optical subsystem includes an exit aperture that is adjustable such that the measurements can be acquired at the multiple AOIs and the multiple azimuthal angles. The exit aperture may be adjusted in any manner known in the art. Collection mirror 24 may include any appropriate reflective optical element known in the art.

Light that is reflected from collection mirror 24 and exits exit aperture 26 is directed to fold mirror 32. Fold mirror 32 may include any appropriate reflective optical element known in the art. Fold mirror 32 directs the light to analyzer 34, which may include any appropriate polarizing component known in the art. In this manner, the reflected light is collected by the collection mirror and directed to the analyzer by the fold mirror. The fold mirror is not an essential part of the system. One may design the system such that the light beam reflected from collection mirror 24 is directed to analyzer 34 without the fold mirror.

Light exiting analyzer 34 is directed to a spectrometer, which includes entrance slit 36, dispersion element 38, and two-dimensional detector 40. In this manner, the light beam is directed to the spectrometer, dispersed, and then directed to a two-dimensional detector, which may be a two-dimensional charge coupled device (CCD) array or any other suitable two-dimensional detector known in the art, that is configured to convert light power signals into electrical signals for processing. Entrance slit 36 may have any suitable configuration known in the art. In addition, dispersion element 38 may include, for example, a prism, gratings, or any other suitable dispersion element known in the art.

As described above, the optical subsystem is configured to collect light scattered from patterned features on the specimen at multiple wavelengths. Therefore, the optical subsystem is configured as a spectroscopic scatterometer. In addition, as described above, the optical subsystem includes rotating polarizer 14 and analyzer 34. The rotating polarizer and the analyzer may be configured such that the optical subsystem is configured as an SE. In one embodiment, therefore, the measurements acquired by the optical subsystem include ellipsometric measurements and SE measurements.

Alternatively, the rotating polarizer and the analyzer may be configured such that the optical subsystem is configured as a spectroscopic reflectometer or a polarized spectroscopic reflectometer. In another embodiment, therefore, the measurements acquired by the optical subsystem include reflectometric measurements (e.g., spectroscopic reflectometric measurements, polarized reflectometric measurements, etc.).

Some aspects of the configuration of the system shown in FIG. 1 make the system embodiment particularly suitable for acquiring the measurements described herein. For instance, as described further above, the system may include a rotating stage, an adjustment mechanism built into the exit aperture (e.g., the adjustable collection mirror), and a two-dimensional detector such that the system can acquire both spectroscopic and angle-resolved measurements of patterned features on a specimen. In addition, the adjustable exit aperture is positioned in front of the collection mirror, which facilitates the angle-resolved spectroscopic measurements and enhanced sensitivity to one or more characteristics of the patterned features on the specimen such as CDs and profile characteristics.

Furthermore, as shown in FIG. 1 and described further herein, in one embodiment, the optical subsystem includes two-dimensional detector 40. In some embodiments, the multiple wavelengths ($\lambda$) are mapped along a first dimension of the detector, and the multiple AOIs and the multiple azimuthal angles ($f(\theta, \phi)$) are mapped along a second dimension of the detector. In this manner, the optical subsystem can acquire measurements of light scattered from the patterned features on the specimen at multiple AOIs, multiple azimuthal angles, and multiple wavelengths simultaneously. In addition, the optical subsystem can acquire measurements of light scattered from the patterned features on the specimen at multiple AOIs, multiple azimuthal angles, and multiple wavelengths simultaneously using a single detector. Therefore, the system shown in FIG. 1 can acquire a substantially large number of measurements in a relatively short amount of time.

The system embodiment shown in FIG. 1 and other system embodiments described herein include a processor such as processor 42 shown in FIG. 1. The processor is configured to determine the one or more characteristics of the patterned features from the measurements. The one or more characteristics may include CD of the patterned features, profile characteristics of the patterned features, any other characteristic(s) described herein or known in the art, or some combination thereof. Processor 42 may be coupled to two-dimensional detector 40 by a transmission medium (not shown). The transmission medium may include any suitable transmission medium known in the art. In addition, the processor may be coupled to the two-dimensional detector by one or more electronic components (not shown) such as an analog-to-digital converter. In this manner, processor 42 is configured to receive measurements from two-dimensional detector 40.

In this manner, processor 42 may be configured to use the measurements received from two-dimensional detector 40 to determine any of the one or more characteristics described herein. In addition, the processor may be configured to use the measurements and any method and/or algorithm known in the art to determine the one or more characteristics. Furthermore, processor 42 may be configured to perform any other metrology-related functions known in the art.

Processor 42 may take various forms, including a personal computer system, mainframe computer system, workstation, image computer, parallel processor, or any other device known in the art. In general, the term "computer system" may be broadly defined to encompass any device having one or more processors, which executes instructions from a memory medium. The system shown in FIG. 1 may be further configured as described herein. The system shown in FIG. 1 has all of the advantages of other embodiments described herein.

The system shown in FIG. 1 and other system embodiments described herein may be use to perform a method for measuring one or more characteristics of patterned features on a specimen. The method may include one or more of the following steps. For example, for a given specimen, from nominal characteristics of its patterned features and film stack structures (e.g., CDs, profile characteristics such as side wall angles, film thicknesses, material optical properties, etc.), the method may include determining whether there are conditions that allow SPWs or guided waves in one or more film layers on the specimen or at any interface within a film stack on the specimen. The conditions that are determined in this step may include the multiple AOIs and the multiple azimuthal angles at which the measurements are performed. In this manner, the conditions that are determined in this step may be used to determine a configuration (e.g., one or more parameters of the rotating stage, one or more parameters of the adjustable collection mirror, etc.) of the optical subsystem that is used to acquire measurements of light scattered from patterned features on the specimen. In some embodiments, therefore, the multiple AOIs and the multiple azimuthal angles at which the optical subsystem acquires measurements of light scattered from patterned features on the specimen are selected such that the measurements of the light include measurements of SPWs and guided waves.

Conditions that excite SPWs, guided waves, or both, may be found for most specimens used in semiconductor fabrication processes. Furthermore, for certain specimens, even if the resonance phenomena (SPWs and guided waves) do not exist, the measurement sensitivity of the spectroscopic scatterometer is still related to the AOIs and azimuthal angles. Therefore, the method may include determining the most sensitive AOIs and azimuthal angles for the measurements, and by providing capabilities to adjust these angles of a measurements system in parallel, the measurements can be performed at the most sensitive AOIs and azimuthal angles thereby optimizing the measurements. For instance, in one embodiment, the one or more characteristics of the patterned features determined from the measurements include CD of the patterned features. In one such embodiment, the multiple AOIs and the multiple azimuthal angles at which the measurements of the light scattered from the patterned features are acquired by the optical subsystem are selected such that the measurements are more sensitive to the CD than if the measurements were acquired at different AOIs and different azimuthal angles. In this manner, the sensitivity of the measurements to CD characteristics may be optimized by varying AOI and azimuthal angle.

The resonance is related to the fact that silicon, the dominant substrate material used in semiconductor manufacturing, has optical properties with the negative real-part of its dielectric constant in the ultraviolet (UV) spectrum below 290 nm. When these conditions exist, the film stack and patterned feature data may be used to solve the dispersion relations for the SPWs or guided waves. These dispersion relations are expressed as functions that define the dependence of propagation constants of SPWs or guided waves on the wavelengths, in relation to optical properties and film thicknesses of each layer in the film stack.

To solve the dispersion relations, one of the following three methods may be used. The first method is the rigorous solution in which rigorous diffraction theories such as rigorous coupled-wave analysis (RCWA) are used to solve Maxwell's equations under boundary conditions. The dispersion relations for SPWs and/or guided waves are then determined. The second method is an approximate solution in which the layer containing patterned features is approximately represented by, for instance, the effective medium model. The third method involves obtaining the time-domain signal via Fourier transform of the spectral signal (frequency domain signal) and identifying the resonance from the time-domain signal. When there is no resonance, the time-domain signal decays exponentially. The existence of resonance results in slower decay in combination with oscillating signals with multiple peaks and valleys.

The method may also include using two-dimensional grating equations or three-dimensional extended grating equations (in which both the in-plane and conical diffraction orders are taken into account) to identify the AOIs and azimuthal angles at which some diffraction orders have tangential components of the wavevector matching those of SPWs or guided waves, leading to the coupling of light power from the incident beam into SPWs, guided waves, or both. This coupling results in concentration of local electromagnetic fields onto certain parts of the patterned features thereby enhancing the sensitivity of the measurements to CD and other profile characteristics of the patterned features. The above described coupling conditions thereby determine the optimum AOIs and azimuthal angles for the measurements. In one embodiment, therefore, the measurements of the light acquired by the optical subsystem embodiments described herein include measurements of SPWs and guided waves. In addition, the one or more characteristics of the patterned features determined from the measurements may include CD of the patterned features. In this manner, the measurements are more sensitive to the CD than if the measurements do not include the measurements of the SPWs and the guided waves.

One or more parameters of the optical subsystem may then be determined based on the results of the above steps. The one or more parameters of the optical subsystem may be used to generate a recipe (i.e., a set of instructions) for acquiring the measurements of the specimen. The one or more parameters of the optical subsystem may then be altered prior to acquisition of the measurements based on the recipe. The one or more parameters of the optical subsystem may be altered by the processor or a control subsystem (not shown) included in the system.

In one embodiment, the method may include rotating the stage to position the specimen under the above optimum azimuthal angle. The method may also include moving the adjustable exit aperture in the direction perpendicular to the incidence plane to further fine tune the azimuthal angle. In addition, the method may include adjusting the length of this aperture in the direction perpendicular to the incidence plane to select the optimum numerical aperture (NA) in the direction perpendicular to the incidence plane. The method may further include moving the adjustable exit aperture in the incidence plane to select the optimum AOI. The method may also include adjusting the width of this aperture in the direction of the incidence plane to select the optimum NA in the direction parallel to the incidence plane. After the parameters of the optical subsystem have been altered, measurements of the light scattered from patterned features on a specimen at multiple AOIs, multiple azimuthal angles, and multiple wavelengths may be acquired simultaneously.

Figure 2:
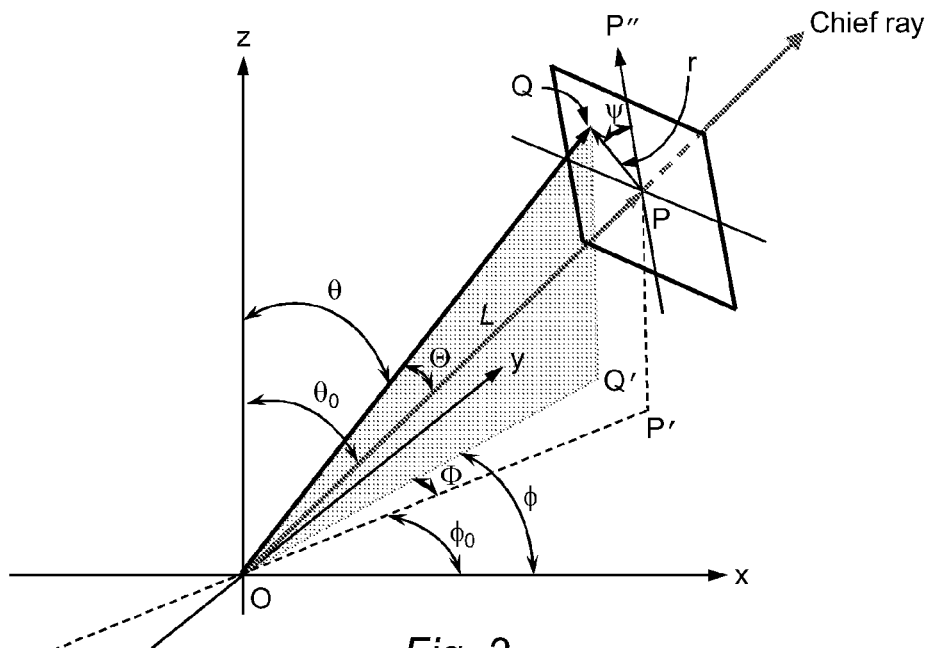
FIG. 2 is a schematic diagram illustrating the geometric relationship for mapping multiple angles of incidence (AOIs) and multiple azimuthal angles to the plane in the exit aperture of an embodiment of an optical subsystem described herein.

One significant advantage of the embodiments described herein is the capability to perform azimuthal angle-resolved spectroscopic measurements. This capability will be fully described in detail in the following figures. For example, FIG. 2 shows the geometrical relationship that can be used to map the AOIs and azimuthal angles to positions in the plane of the exit aperture of an angle-resolved spectroscopic ellipsometer. In this manner, FIG. 2 illustrates how angle-resolved (either AOI or azimuthal angle) spectroscopic measurements can be performed. As shown in FIG. 2, the chief ray in the incidence plane defines the main AOI ($\theta_0$) and azimuthal angle ($\phi_0$). Any ray in the reflection light cone falls onto the exit aperture at a position represented by the polar coordinates (r, $\psi$).

It is noted that the coordinate systems shown in FIG. 2 are referenced to the grating or three-dimensional patterned features on the specimen under test. Using a grating as an example, the x-direction of the coordinate systems is in the direction perpendicular to the grating lines, the y-direction is parallel to the grating lines, and the z-direction is perpendicular to the grating plane. As a result, if the plane of incidence of the optical subsystem is aligned with the x-direction, then angle $\phi_0$ in FIG. 2 is zero. In other words, the azimuthal angle of the measurement system is set to zero. One additional observation is that this "zero" azimuthal angle corresponds to the chief ray of the optical subsystem. In practice, the illumination and reflection beams both have finite NA, and the other rays in the light cone may have non-zero azimuthal angles. Another additional observation is that in practical applications a non-zero azimuthal angle may intentionally be used for the optical subsystem to enhance sensitivity of the measurements as described further herein.

Figure 3:
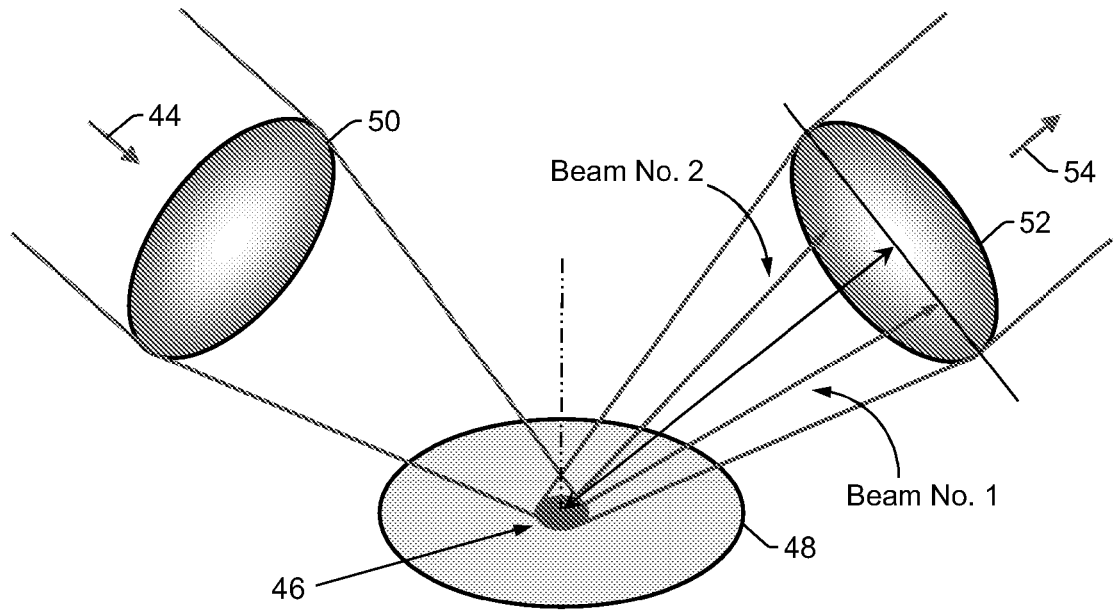
FIG. 3 is a schematic diagram illustrating a perspective view of two beams reflected from a specimen, which represent the in-plane and out-of-plane reflection conditions with different AOIs and different azimuthal angles.
Figure 4:
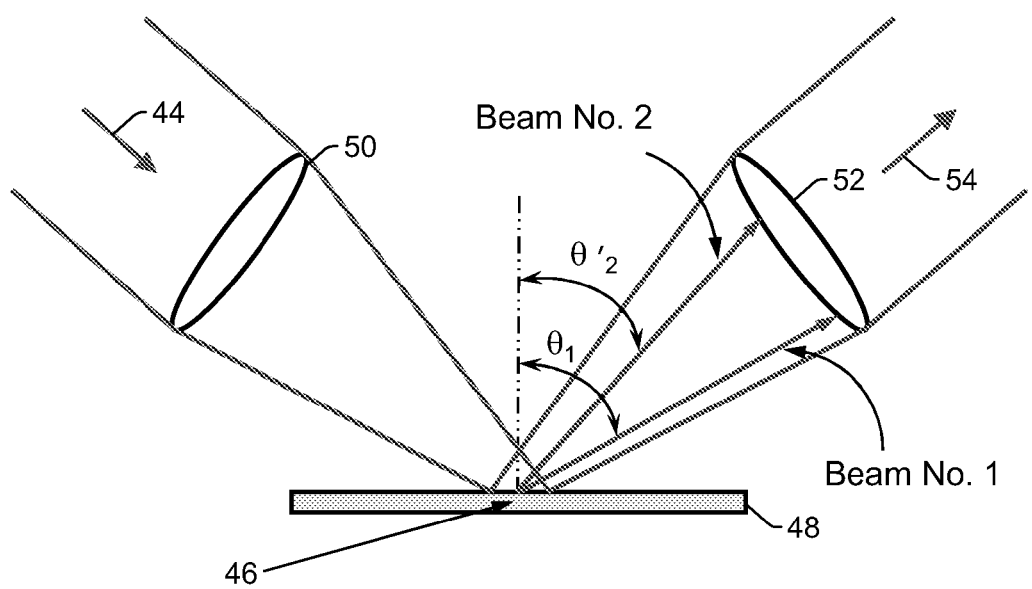
FIG. 4 is a schematic diagram of a side view of FIG. 3, which illustrates the in-plane angles of the two beams (projection of the AOIs of the two beams onto the incidence plane)
Figure 5:
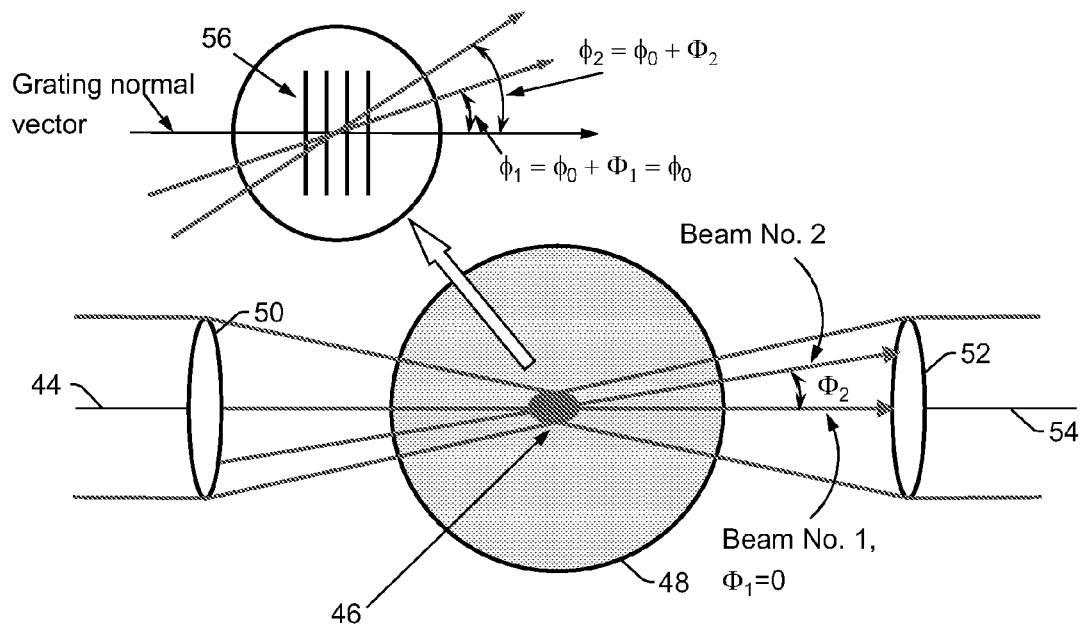
FIG. 5 is a schematic diagram of a top view of FIG. 3, which illustrates the geometric relationship that defines the azimuthal angles of the two beams.

FIGS. 3-5 provide further illustration of the angular relationships described above. In particular, FIG. 3 illustrates a portion of an embodiment of an angle-resolved spectroscopic measurement system. FIG. 3 also illustrates two reflection beams that represent the in-plane (Beam No. 1) and out-of-plane (Beam No. 2) reflection conditions with different AOIs and azimuthal angles. In the system shown in FIG. 3, light 44 from a light source (not shown in FIG. 3) such as a light source described further herein may be directed to illuminated spot 46 on specimen 48 by focusing optics 50. Focusing optics 50 may include a refractive optical element as shown in FIG. 3. However, focusing optics 50 may include a focusing mirror as described above. In addition, focusing optics 50 may include one or more refractive optical elements and/or one or more reflective optical elements. Light scattered from specimen 48 including Beam No. 1 and Beam No. 2 is collected by collection optics 52. Collection optics 52 may be a refractive optical element as shown in FIG. 3. However, collection optics 52 may be configured as shown in FIG. 1 and described further herein. Light 54 collected by the collection optics is directed to a detector (not shown in FIG. 3) such as a detector described further herein.

FIG. 4 shows the side view of FIG. 3, illustrating the in-plane angles (projection of AOIs onto the incidence plane). FIG. 5 shows the top view of FIG. 3, illustrating the geometric relationships that define azimuthal angles. The angle $\phi_0$ shown in FIG. 5 is the same as angle $\phi_0$ illustrated in FIG. 2, to indicate the angle the plane of incidence makes with the x-direction of the coordinate system (the direction perpendicular to grating lines 56 shown in FIG. 5). To illustrate the azimuthal angle relationship, FIG. 5 further shows two typical rays in the light cones with azimuthal angle $\phi_1$ and $\phi_2$, which are measured from the x-direction. In practice, the azimuthal angles are measured from the plane of incidence. As a result, one first determines the angular position of the plane of incidence (i.e., the $\phi_0$ angle, which may also be commonly referred to as the "azimuthal angle calibration"), then the relative angular positions of these typical rays are measured from the plane of incidence (the $\Phi_1$ and $\Phi_2$ angles shown in FIG. 5). Adding the $\phi_0$ angle to the relative angles $\Phi_1$ and $\Phi_2$ one obtains the absolute azimuthal angles $\phi_1$ and $\phi_2$, as shown in FIG. 5.

Figure 6:
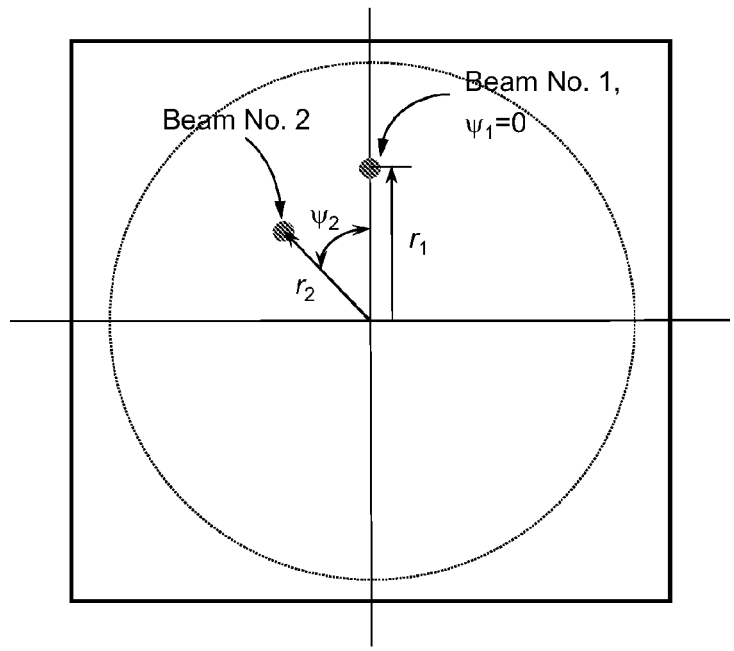
FIG. 6 is a schematic diagram illustrating a cross-sectional view of the plane of an exit aperture of an optical subsystem and a position of the two beams illustrated in FIG. 3 on the plane.

FIG. 6 shows the positions of the reflection beams on the plane of the exit aperture of an angle-resolved spectroscopic measurement system, which defines the geometric relationship that can be used to calculate AOIs and azimuthal angles for the reflection beams.

Referring back to FIG. 2, the AOI and azimuthal angle can be calculated from the coordinates (r, $\psi$) and the angular position of the chief ray, (L, $\theta_0$, $\phi_0$). From FIG. 6, the Cartesian coordinates of the chief ray are given by $$L = \overrightarrow{OP} = (L \sin\theta_0 \cos\phi_0, L \sin\theta_0 \sin\phi_0, L\cos\theta_0) \quad (1)$$

Further, from FIG. 6, point Q, at which the reflection ray falls onto the exit aperture, is determined by the polar coordinates (R, $\theta$, $\phi$) which are related to Cartesian coordinates by $$R = \overrightarrow{OQ} = (R\sin\theta\cos\phi, R\sin\theta\sin\phi, R\cos\theta) \quad (2)$$

Obviously, we have $$R = |\overrightarrow{OQ}| = \sqrt{L^2 + r^2} \quad (3)$$

Furthermore, we may determine the other related vectors $$r = \overrightarrow{PQ} = R - L = (R\sin\theta\cos\phi - L\sin\theta_0\cos\phi_0, R\sin\theta\cos\phi - L\sin\theta_0\sin\phi_0, R\cos\theta - L\cos\theta_0)$$

$$\overrightarrow{PP''} = (-\cos\theta_0\cos\phi_0, -\cos\theta_0\sin\phi_0, \sin\theta_0) \quad (4)$$

where $\overrightarrow{L} \cdot \overrightarrow{PP''} = 0$. The AOI and azimuthal angle of the ray $R = \overrightarrow{OQ}$ can be solved using the relations $$\cos\Theta = \frac{L \cdot R}{LR} \quad (5)$$
$$= \sin\theta_0\cos\phi_0\sin\theta\cos\phi + \sin\theta_0\sin\phi_0\sin\theta\sin\phi_0 + \cos\theta_0\cos\theta$$
$$= \frac{L}{R}$$

$$\cos\psi = \frac{r \cdot \overrightarrow{PP''}}{r}$$
$$= \frac{1}{r}\begin{bmatrix} -\cos\theta_0\cos\phi_0(R\sin\theta\cos\phi - L\sin\theta_0\cos\phi_0) - \\ \cos\theta_0\sin\phi_0(R\sin\theta\sin\phi - L\sin\theta_0\sin\phi_0) + \\ \sin\theta_0(R\cos\theta - L\cos\theta_0) \end{bmatrix}$$

These equations can be solved for ($\theta$, $\phi$), the AOI and azimuthal angle of the ray $R = \overrightarrow{OQ}$. First, the AOI can be determined as $$\cos\theta = \frac{L\cos\theta_0 + r\cos\psi\sin\theta_0}{R} = \frac{L\cos\theta_0 + r\cos\psi\sin\theta_0}{\sqrt{L^2 + r^2}} \quad (6)$$

which satisfies the geometric relationship $$R\cos\theta - L\cos\theta_0 = r\cos\psi\sin\theta_0 \quad (7)$$

Furthermore, the azimuthal angle is then calculated as $$\cos\Phi = \cos(\phi - \phi_0) \quad (8)$$
$$= \frac{L - R\cos\theta_0\cos\theta}{R\sin\theta_0\sin\theta}$$
$$= \frac{L\sin\theta_0 - r\cos\psi\cos\theta_0}{R\sin\theta}$$

-continued $$= \frac{L\sin\theta_0 - r\cos\psi\cos\theta_0}{\sqrt{L^2 + r^2}\sin\theta}$$

which meets the condition that the chief ray and the exit aperture are perpendicular to each other, $$\vec{OP} \cdot \vec{PQ} = L\sin\theta_0\cos\phi_0(R\sin\theta\cos\phi - L\sin\theta_0\cos\phi_0) + \quad (9)$$
$$L\sin\theta_0\sin\phi_0(R\sin\theta\sin\phi - L\sin\theta_0\sin\phi_0) +$$
$$L\cos\theta_0(R\cos\theta - L\cos\theta_0)$$
$$= 0$$

Figure 7:
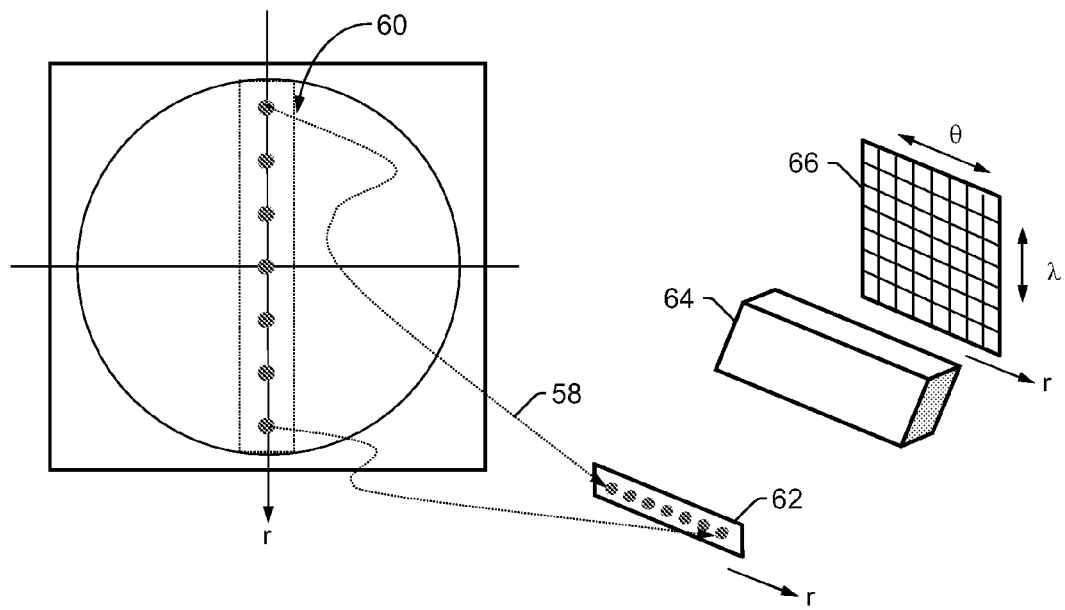
FIG. 7 is a schematic diagram illustrating one example of a portion of an AOI-resolved spectroscopic measurement system.

Using Equations (6) and (8), either AOI-resolved or azimuthal angle-resolved spectroscopic measurement systems can be simply designed. FIG. 7 illustrates one example of a portion of an AOI-resolved spectroscopic measurement system. As shown in FIG. 7, light 58 from exit aperture 60 is directed to spectrometer entrance slit 62. Light exiting the spectrometer entrance slit is directed to dispersive element 64 such as a prism or gratings. Light exiting the dispersive element is directed to two-dimensional detector 66. Each of the elements of the system shown in FIG. 7 may be further configured as described herein.

As shown in Equation (6), the polar angle $\psi$ may be fixed in the plane of exit aperture 60. Then, the AOI depends only on the radial position r of the reflection beam on the plane of the exit aperture. As a result, two-dimensional detector 66, such as a CCD, for instance, may be used to perform the AOI-resolved spectroscopic measurements. For instance, as shown in FIG. 7, the columns in the two-dimensional detector are used to measure angular positions ($\theta$), and the rows are used to record spectral data ($\lambda$). As further shown in FIG. 7, each column in the two-dimensional detector is in conjugate with a point at entrance slit 62 of the spectrometer, which in turn is mapped to one point in the plane of exit aperture 60. All of the columns in two-dimensional detector 66 are in conjugate with entrance slit 62 of the spectrometer, which is in conjugate with one of the diameters in exit aperture 60. FIG. 7 shows one example of a diameter in the plane of incidence of the exit aperture that may be in conjugate with the entrance slit. The diameter shown in FIG. 7, however, should not be considered a limiting example. In fact, any one of the diameters in the exit aperture corresponds to a specific set of AOIs at a fixed azimuthal angle, as shown in Equation (6). Furthermore, this system can be used for cases in which the chief ray is at a normal AOI or when the chief ray is at an oblique AOI.

Figure 8:
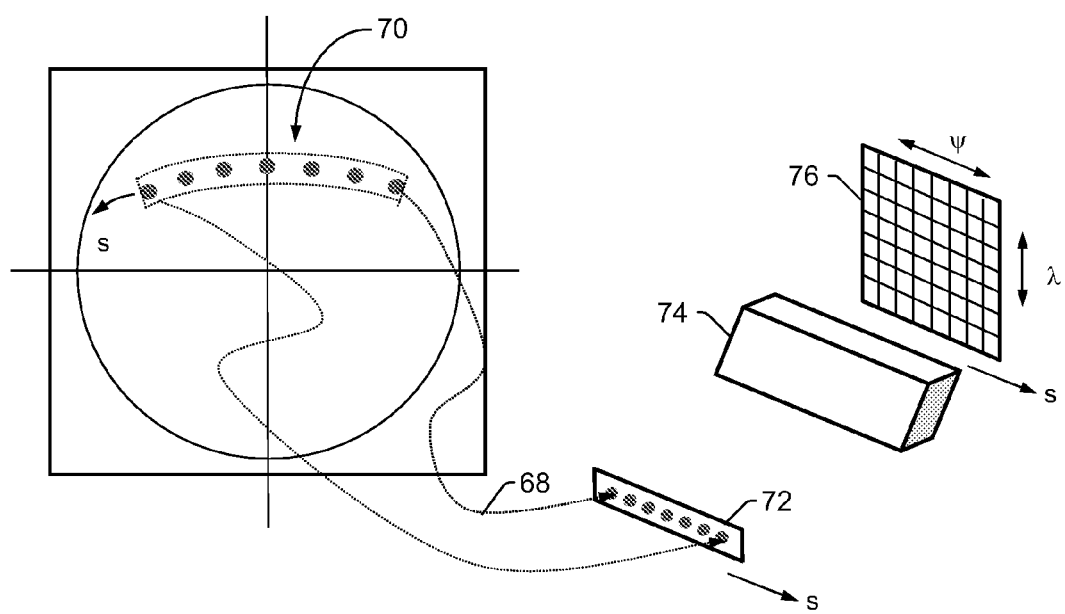
FIG. 8 is a schematic diagram illustrating one example of a portion of an azimuthal angle-resolved spectroscopic measurement system.

FIG. 8 illustrates one example of a portion of an azimuthal angle-resolved spectroscopic measurement system. As shown in FIG. 8, light 68 from exit aperture 70 is directed to spectrometer entrance slit 72. Light exiting the spectrometer entrance slit is directed to dispersive element 74 such as a prism or gratings. Light exiting the dispersive element is directed to two-dimensional detector 76. Each of the elements of the system shown in FIG. 8 may be further configured as described herein.

According to Equations (6) and (8), azimuthal angle, $\phi$, depends on both the radial and polar angle coordinates in the exit aperture. As a result, beams with different azimuthal angles $\phi$ will fall onto a curve, instead of a line, in the plane of the exit aperture, as shown in FIG. 8. To map a curve in the exit aperture to a line in the entrance slit of the spectrometer, a special optical subsystem needs to be designed for this purpose. One of the solutions for such an optical subsystem is to use an optical fiber bundle, which can easily fulfill the above requirement. One of the trade-offs of using a fiber bundle is the transmission cut-off of the optical fibers, which limit the spectrum in the UV. In particular, the spectrum below 250 nm is usually noisy when fibers are used to guide light.

Two-dimensional detector 76, such as a CCD, for instance, may be used to perform the azimuthal angle-resolved spectroscopic measurements. For instance, as shown in FIG. 8, the columns in the two-dimensional detector are used to measure angular positions ($\psi$), and the rows are used to record spectral data ($\lambda$). As further shown in FIG. 8, each column in the two-dimensional detector is in conjugate with a point at entrance slit 72 of the spectrometer, which in turn is mapped to one point in the plane of exit aperture 70. In this manner, all of the columns in two-dimensional detector 76 are in conjugate with entrance slit 72 of the spectrometer, which is in conjugate with one of the curves in exit aperture 70. FIG. 8 shows one example of a curve in the plane of incidence of the exit aperture that may be in conjugate with the entrance slit. The curve shown in FIG. 8, however, should not be considered a limiting example. Furthermore, this system can be used for cases in which the chief ray is at a normal AOI or when the chief ray is at an oblique AOI.

Another method to facilitate azimuthal angle-resolved spectroscopic measurements includes using a few (e.g., two or more) monochromatic light sources, which generate light at discrete wavelengths, in combination with time-domain multiplexing (TDM). One typical implementation of this method is to configure the optical subsystem such that the chief ray of illumination is at normal incidence. Under these conditions, the azimuthal angle $\phi$ is simply mapped to the polar angle $\psi$ in plane of the exit aperture. When a two-dimensional detector array is used to record the signals, rays with various AOIs and azimuthal angles are mapped to pixels in different rows and columns. TDM enables the spectroscopic measurements by "turning on" each light source in a time sequence. As a result, at a given moment, the two-dimensional detector (e.g., a CCD array) will record reflection signals with various AOIs and azimuthal angles at one specific wavelength. A time scan results in a data cube of ($\lambda$, $\theta$, $\phi$). There are two drawbacks of this method. First, obviously, the measurement throughput is reduced. And second, the number of wavelengths available for measurements is limited.

Figure 9:
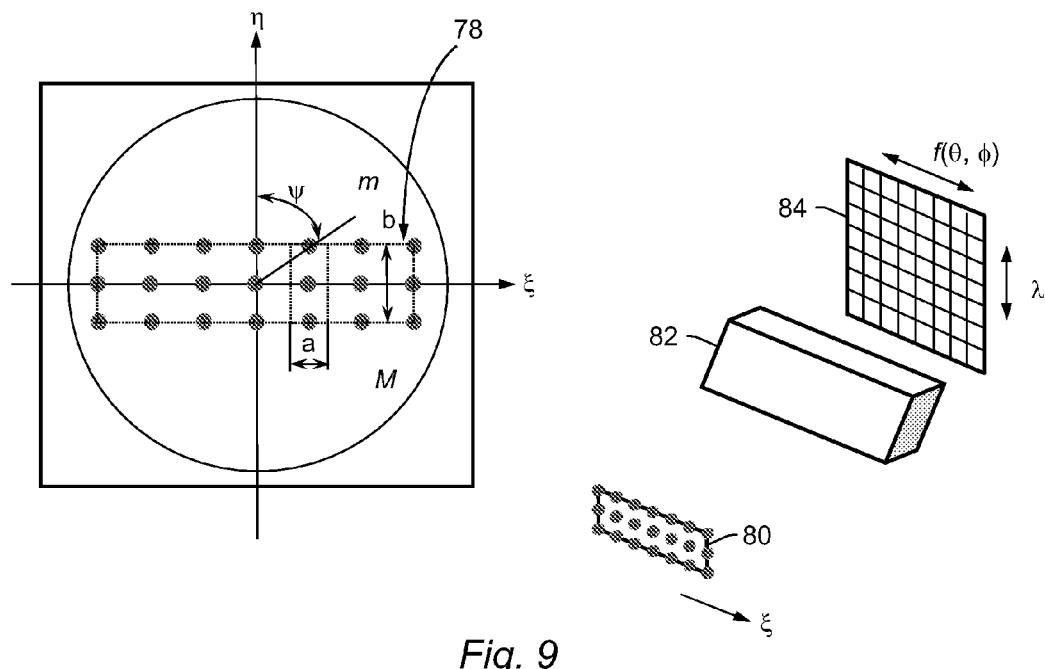
FIG. 9 is a schematic diagram illustrating one embodiment of a portion of an optical subsystem that may be included in a system embodiment described herein.

FIG. 9 illustrates one embodiment of a portion of a system configured to measure one or more characteristics of patterned features on a specimen. The system shown in FIG. 9 enables azimuthal angle-resolved spectroscopic measurements without the above disadvantages. In particular, as shown in FIG. 9, the optical subsystem includes exit aperture 78. In one embodiment, as shown in FIG. 9, the multiple AOIs and the multiple azimuthal angles are mapped across two dimensions of exit aperture 78. In particular, the multiple AOIs are mapped across the dimension of the exit aperture parallel to the direction of the width b of the exit aperture. In addition, the multiple azimuthal angles are mapped across both dimensions of the exit aperture. In other words, the azimuthal angles vary across the width b of the exit aperture and the length of the exit aperture, which is in the direction perpendicular to the width of the exit aperture. As described further above, the exit aperture may be adjustable such that the measurements can be acquired at the multiple AOIs and the multiple azimuthal angles. For example, the exit aperture may be adjusted based on characteristics of the specimen and the characteristics of the specimen that are to be measured, which can be used to select the multiple AOIs and the multiple azimuthal angles at which the measurements are performed as described further herein. The exit aperture can be adjusted based on the multiple AOIs and the multiple azimuthal angles as described further herein.

The optical subsystem includes spectrometer entrance slit 80. The spectrometer entrance slit is in conjugate with exit aperture 78 such that the multiple AOIs and the multiple azimuthal angles are mapped across two dimensions of the entrance slit. The entrance slit of the spectrometer may be further configured as described herein. The optical subsystem also includes dispersive element 82 of the spectrometer, which may include for example a prism or gratings. The dispersive element is positioned in the path of the light exiting entrance slit 80. The dispersive element may be further configured as described herein.

As further shown in FIG. 9, the optical subsystem may include two-dimensional detector 84 of the spectrometer. In some embodiments, the two-dimensional detector may be a two-dimensional CCD. However, the two-dimensional detector may include any appropriate two-dimensional detector known in the art. In one embodiment, the multiple wavelengths are mapped along a first dimension of the detector, and the multiple AOIs and the multiple azimuthal angles are mapped along a second dimension of the detector. Therefore, the two dimensions of the exit aperture (across which the light varies as a function of AOI and azimuthal angle) are mapped across one dimension of the two-dimensional detector such that the wavelength can be mapped across the other dimension of the detector thereby enabling measurements at multiple AOIs, multiple azimuthal angles, and multiple wavelengths simultaneously by a single detector.

In one such embodiment, the optical subsystem includes exit aperture 78, two-dimensional detector 84, and a set of optical fibers (not shown). As described above, the multiple AOIs and the multiple azimuthal angles are mapped across two dimensions of the exit aperture, and the multiple AOIs and the multiple azimuthal angles are mapped along one dimension of the detector. In one such embodiment, the set of optical fibers is configured to direct light from the two dimensions of the exit aperture to the one dimension of the detector. For example, the set of optical fibers may be positioned between the exit aperture and the entrance slit or between the entrance slit and the dispersive element. The set of optical fibers may include any appropriate optical fibers known in the art. Two-dimensional detector 84 may be further configured as described herein.

As described above, the optimum conditions for AOI and azimuthal angle may be determined by identifying the conditions to excite and couple light into SPWs and/or guided waves. Altering the azimuthal angle of the optical subsystem to the optimal azimuthal angle used for the measurements can be facilitated by the rotating stage. However, in practical applications, azimuthal angle-resolved measurements may be desired in addition to the rotating stage capability for setting the optimal azimuthal angle.

In some embodiments, the multiple AOIs are selected based on an optimal AOI and potential variations in the one or more characteristics of the patterned features. In some such embodiments or in other embodiments, the multiple azimuthal angles are selected based on the optimal azimuthal angle and the potential variations in the one or more characteristics of the patterned features. For example, in practical manufacturing, process conditions such as focus, exposure, photoresist composition, spin-coating speed, post-exposure bake (PEB) temperature, etc. may fluctuate thereby causing process variations. As a result, patterned features printed by the process will also change with CD variations, underlayer thickness changes, or both. In fact, one of the most important purposes of semiconductor metrology is to control process variations to enhance manufacturing yield.

These process variation induced CD or film thickness changes will inevitably shift the optimum AOI and azimuthal angle for sensitivity enhancement of the measurements. On the other hand, to measure CD and thickness variations across an entire specimen, a specimen is typically measured at multiple places (which are commonly referred to as "measurement sites" in a "wafer map"). For practical measurements, a "recipe" is created that defines measurement conditions such as the AOI and azimuthal angle for all measurement sites. Because of the above described CD and thickness variations, the optimum AOI and azimuthal angle may change slightly from one site to another. For practical measurement purposes, especially when measurement throughput is one of the main tool specifications, an angle-resolved measurement system is desirable such that measurements can be performed across certain ranges of AOI and azimuthal angle to cover the entire "process window."

Such measurements may be performed as follows. First, based on nominal film stack and CD/profile characteristics, the optimum AOI and azimuthal angle that will maximize the sensitivity of the measurements can be determined. As shown in FIG. 1, parameters of the exit aperture such as the position and the length/width of the exit aperture are adjustable. Then, by rotating the stage and adjusting the position of the exit aperture, the chief ray can be positioned at the above optimum angles ($\theta_0$, $\phi_0$). On the other hand, the process window, or the set of possible ranges of CDs and profile characteristics as well as underlayer film thicknesses variations, is predetermined in practical fabrication processes. As such, the length and width of the exit aperture can be altered accordingly.

In some embodiments, the measurements at the multiple AOIs and the multiple azimuthal angles are averaged over a portion of the NA of the optical subsystem. For example, any optical measurement system has a finite angular exit aperture, which determines the power the detector will receive. As a result, practical measurements are not performed at exactly one AOI and one azimuthal angle; instead, the measurements are conducted within finite ranges of AOI and azimuthal angle, and the integrated power corresponding to this finite light cone is recorded. This condition is commonly termed "NA average" in metrology. In this manner, the embodiments described herein can use an "NA average" method to perform AOI- and azimuthal angle-resolved spectroscopic measurements. Given this, it is possible to design a system which will perform "NA average" measurements within a range of AOI and azimuthal angle for our purpose of optimizing CD and profile sensitivity.

In some embodiments, the optical subsystem includes a two-dimensional detector (e.g., two-dimensional detector 84 shown in FIG. 9) that is electronically adjustable such that the measurements can be acquired at the multiple AOIs and the multiple azimuthal angles. As shown in FIG. 9, for example, the columns of the two-dimensional detector are mapped to the entrance slit of the spectrometer, which in turn is imaged to the exit aperture for angle-resolved measurements. The rows of the two-dimensional detector can then be used to resolve for wavelength.

As an example, let us consider a two-dimensional detector that has 128 columns and 1024 rows. Referring to FIG. 9, the range for AOI average is completely determined by the width (w) of the exit aperture. On the other hand, the total number of azimuthal angles and the range for azimuthal angle average are determined by both the length (b) of the exit aperture and the width (a) of each "sub-aperture" of the exit aperture. These sub-apertures are flexible both in numbers (which in turn determine how many azimuthal angles are resolved) and in width and can be adjusted electronically.

For example, in standard CCD read-out circuit design, all 128 columns can be resolved, which in turn gives a total of 128 azimuthal angle-resolved measurements. In the other extreme, all 128 columns can be averaged and taken as one single measurement, which is used as a representative of the signal corresponding to the chief ray. In between these extremes, an electronic read-out circuit can be configured to allow for instance, a total of 8, 16, or 32 sub-apertures, which in turn averages across 16, 8, or 4 columns, respectively, to generate signals corresponding to one sub-aperture, and the width a of the sub-aperture is determined accordingly. Given the values of (a, b) and the center position of each sub-aperture, one can integrate the reflection signals across $(\theta, \phi)$ calculated from Equations (6) and (8) and falling within the sub-aperture to perform the standard "NA average." The portion of the system shown in FIG. 9 may be further configured as described herein. In addition, the system shown in FIG. 9 has all of the advantages of other embodiments described herein.

FIGS. 10-13 illustrate various embodiments of a system configured to measure one or more characteristics of patterned features on a specimen. It is to be understood that these embodiments illustrate the principle disclosed in FIG. 9, which is the use of optical subsystems with two foci for the formation of "two images," one to resolve for spectral dispersion, and another to resolve for AOI, azimuthal angle, or the combination of AOI and azimuthal angle. In particular, the systems shown in FIGS. 10-13 include optical subsystems that are configured to acquire measurements of light scattered from patterned features on a specimen at multiple AOIs, multiple azimuthal angles, and multiple wavelengths simultaneously.

Figure 10:
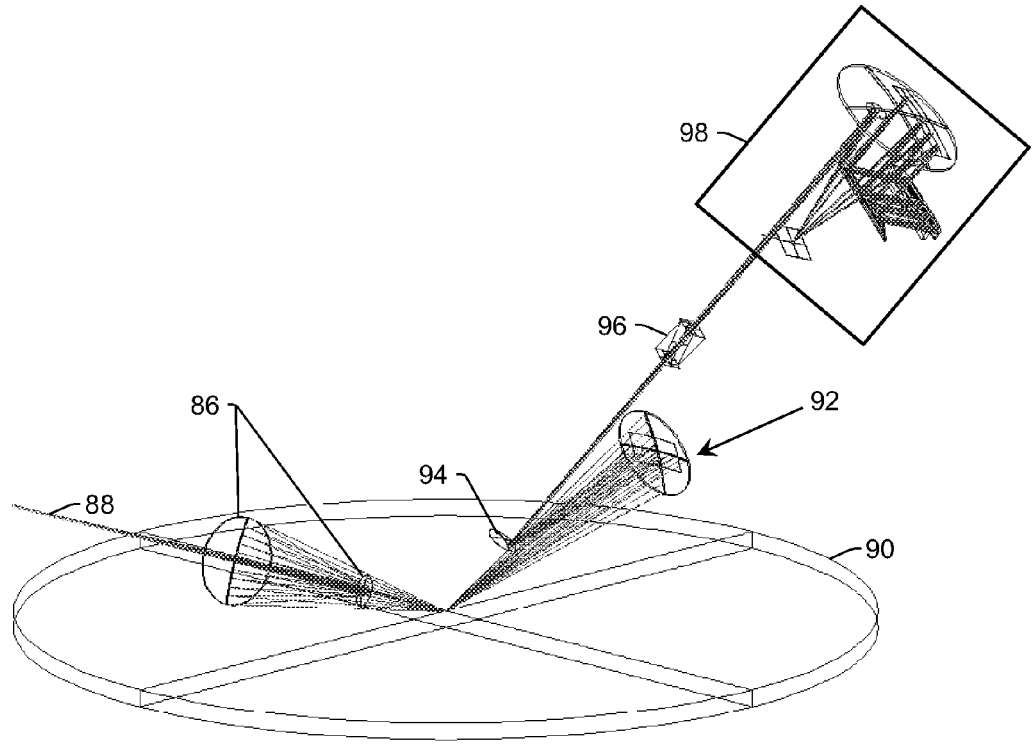
FIGS. 10-13 are schematic diagrams illustrating a side view of various embodiments of a portion of an optical subsystem that may be included in a system embodiment described herein.

As shown in FIG. 10, one embodiment of the optical subsystem includes focusing mirrors 86 configured to direct light 88 to specimen 90. The focusing mirrors may be further configured as described herein. In addition, light 88 may be generated by a light source (not shown in FIG. 10) including any of the light sources described herein. The optical subsystem also includes collection mirrors 92 and 94 that are configured to collect light scattered from the patterned features on the specimen. In the embodiment shown in FIG. 10, collection mirror 92 is a toroidal mirror that has $r_x$=95.600 and $r_y$=95.108. The collection mirrors may be further configured as described herein. The optical subsystem further includes analyzer 96. Collection mirror 94 directs the collected light to analyzer 96, which may be configured as described herein. In addition, the optical subsystem includes spectrometer 98. Light exiting analyzer 96 is directed to spectrometer 98, which may be configured as described herein. The system shown in FIG. 10 may be further configured as described herein and has all of the advantages of other embodiments described herein.

Figure 11:
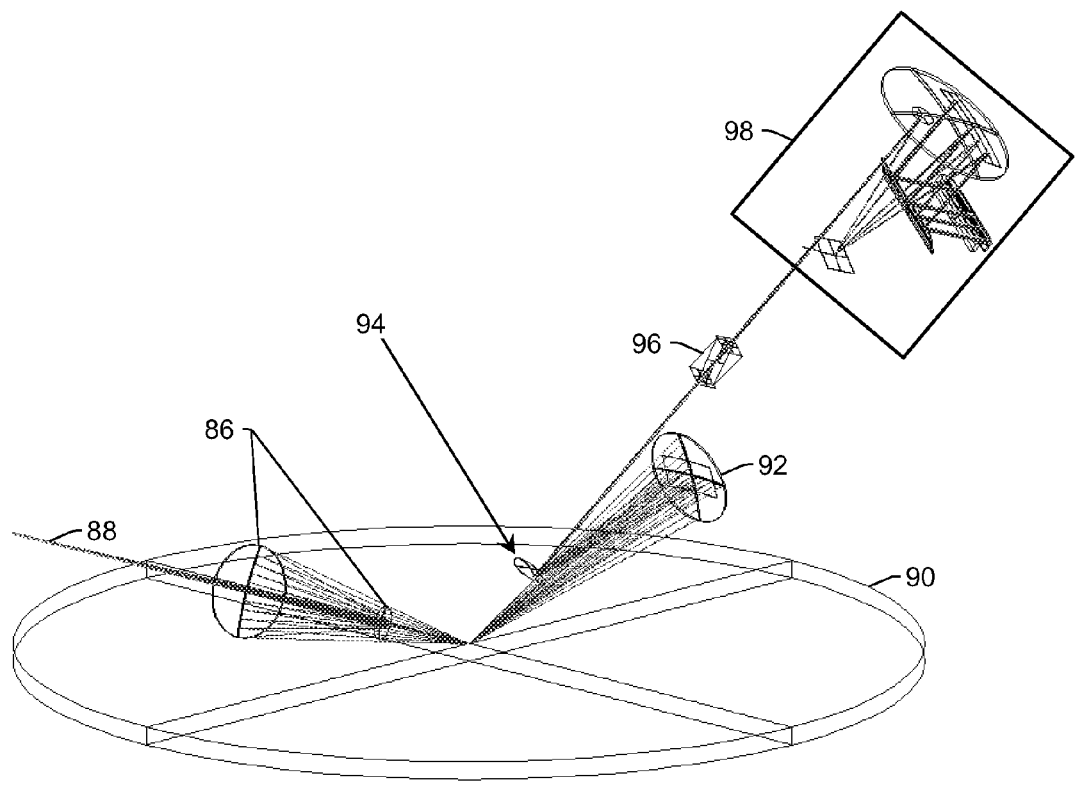

As shown in FIG. 11, another embodiment of the optical subsystem includes focusing mirrors 86 configured to direct light 88 to specimen 90. The focusing mirrors may be further configured as described herein. In addition, light 88 may be generated by a light source (not shown in FIG. 11) including any of the light sources described herein. The optical subsystem also includes collection mirrors 92 and 94 that are configured to collect light scattered from the patterned features on the specimen. In the embodiment shown in FIG. 11, collection mirror 94 is a toroidal mirror that has $r_x$=16.500 and $r_y$=17.202. The collection mirrors may be further configured as described herein. The optical subsystem further includes analyzer 96. Collection mirror 94 directs the collected light to analyzer 96, which may be configured as described herein. In addition, the optical subsystem includes spectrometer 98. Light exiting analyzer 96 is directed to spectrometer 98, which may be configured as described herein. The system shown in FIG. 11 may be further configured as described herein and has all of the advantages of other embodiments described herein.

Figure 12:
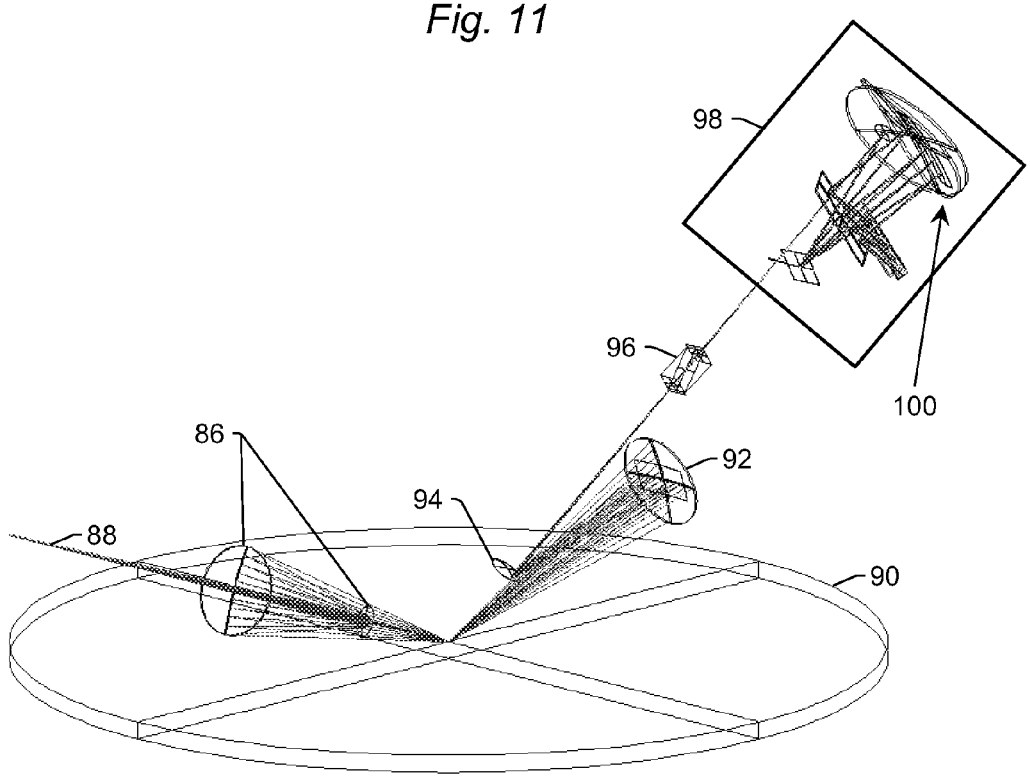

As shown in FIG. 12, an additional embodiment of the optical subsystem includes focusing mirrors 86 configured to direct light 88 to specimen 90. The focusing mirrors may be further configured as described herein. In addition, light 88 may be generated by a light source (not shown in FIG. 12) including any of the light sources described herein. The optical subsystem also includes collection mirrors 92 and 94 that are configured to collect light scattered from the patterned features on the specimen. The collection mirrors may be further configured as described herein. The optical subsystem further includes analyzer 96. Collection mirror 94 directs the collected light to analyzer 96, which may be configured as described herein. In addition, the optical subsystem includes spectrometer 98. Light exiting analyzer 96 is directed to spectrometer 98. In the embodiment shown in FIG. 12, mirror 100 of spectrometer 98 is a toroidal mirror that has $r_x$=−200 and $r_y$=128.8. The spectrometer may be further configured as described herein. The system shown in FIG. 12 may be further configured as described herein and has all of the advantages of other embodiments described herein.

Figure 13:
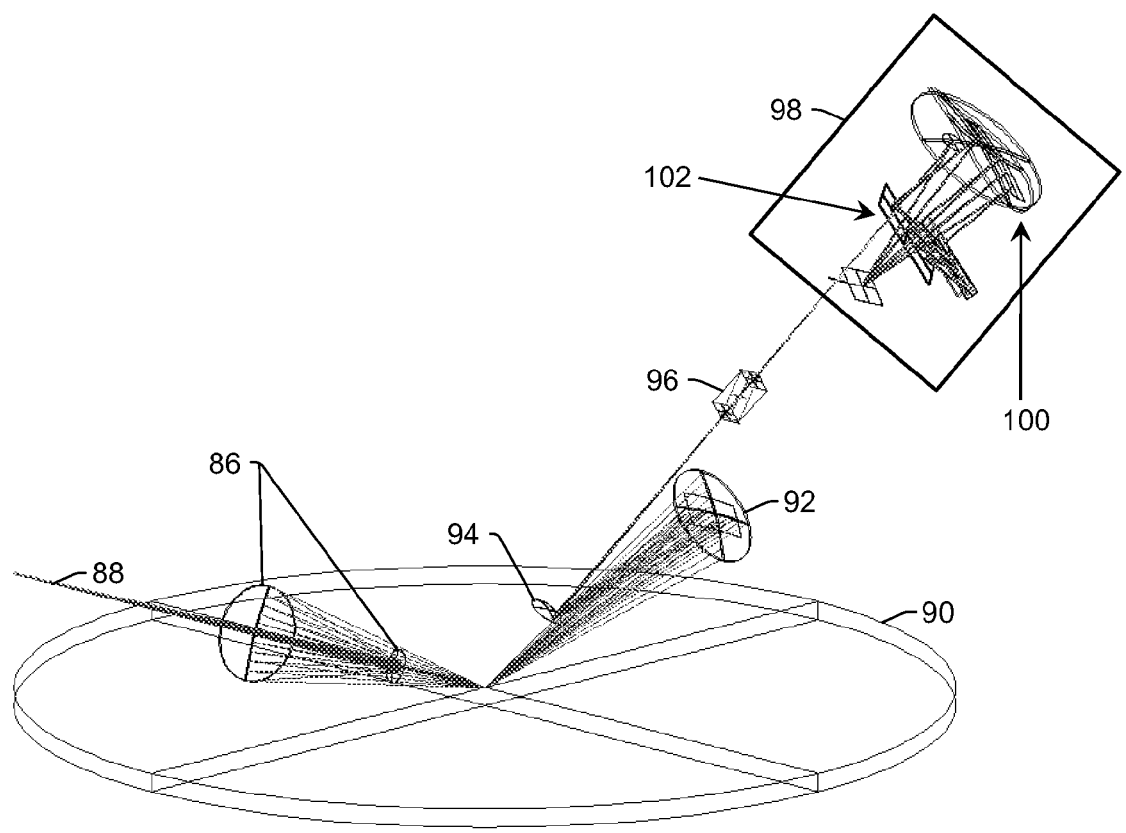

As shown in FIG. 13, a further embodiment of the optical subsystem includes focusing mirrors 86 configured to direct light 88 to specimen 90. The focusing mirrors may be further configured as described herein. In addition, light 88 may be generated by a light source (not shown in FIG. 13) including any of the light sources described herein. The optical subsystem also includes collection mirrors 92 and 94 that are configured to collect light scattered from the patterned features on the specimen. The collection mirrors may be further configured as described herein. The optical subsystem further includes analyzer 96. Collection mirror 94 directs the collected light to analyzer 96, which may be configured as described herein. In addition, the optical subsystem includes spectrometer 98. Light exiting analyzer 96 is directed to spectrometer 98. In the embodiment shown in FIG. 13, mirror 100 of spectrometer 98 is a toroidal mirror that has $r_x$=128.8 and $r_y$=−200. In addition, mirror 102 of the spectrometer is a cylinder mirror that has $r_x$=−150 and $r_y$=Infinity. The spectrometer may be further configured as described herein. The system shown in FIG. 13 may be further configured as described herein and has all of the advantages of other embodiments described herein.

The toroidal mirrors included in the embodiments shown in FIGS. 10-13 are for illustration purpose only to demonstrate the concept of angle-resolved spectral measurements. It should be understood that the optical subsystems shown in FIGS. 10-13 may include practical implementations such as, but not limited to, a toroidal mirror, a combination of a spherical mirror and a cylinder mirror, a combination of a lens and a cylinder mirror, and a combination of a spherical mirror and a cylinder lens.

One important advantage of the embodiments described herein is significantly enhanced sensitivity for measuring one or more characteristics of patterned features having relatively small CDs ahead of leading-edge technologies for extremely challenging layers. For example, such patterned features include patterned features having substantially small CDs (below about 45 nm) and relatively large period (about 700 nm). As described above, the embodiments described herein allow fine-tuning of the measurement conditions (AOI, azimuthal angle) to excite SPWs thereby maximizing the sensitivity to CDs and profile characteristics.

Still another advantage is related to measurements of the light scattered from the patterned features that include measurements of SPWs. For example, in one embodiment, the measurements of the light are responsive to surface plasmon induced depolarization of the light. In one such embodiment, the one or more characteristics of the patterned features that are determined from the measurements include CD and profile of the patterned features. In such an embodiment, the measurements are more sensitive to the CD and the profile than measurements that are not responsive to the surface plasmon induced depolarization. In this manner, the embodiments described herein can use surface plasmon induced depolarization to further enhance sensitivity to CD and profile characteristics.

In particular, as disclosed by C. Genet et al., "Depolarization induced by subwavelength metal hole arrays," arXiv: physics/0311137 v1 28 Nov. 2003, which is incorporated by reference as if fully set forth herein, in addition to significantly enhanced SE signals, the excitation of surface plasmon will cause depolarization if the illumination and collection are conducted with finite angles extended in AOI, azimuthal angle, or in both. Under these conditions, the excitation of surface plasmon, in addition to varying spectral distribution of the light leaving the specimen (either reflected or transmitted), enhances the sensitivity of scattered light signals to the patterned features of the specimen being illuminated and generates additional quantities, the spectral depolarization factors, which can be measured by SE. The surface plasmon induced depolarization depends on the angular extension, or the NAs in the AOI direction and the azimuthal angle direction, of the illumination and collection. Because the embodiments described herein enable the adjustment of AOI, azimuthal angle, as well as the NAs in both directions, this attribute of surface plasmon provides an additional way to enhance the sensitivity.

A still further advantage of the embodiments described herein is the capability to measure line edge roughness (LER). For example, in one embodiment, the one or more characteristics of the patterned features determined by the system include LER of the patterned features. In one such embodiment, the processor is configured to determine the LER by determining surface plasmon induced depolarization of the light and LER induced depolarization of the light using the measurements at the multiple AOIs and the multiple azimuthal angles. In this manner, the embodiments described herein can use AOI and azimuthal angle variations to separate surface plasmon induced depolarization from surface roughness and LER induced depolarization thereby enabling the measurement of LER.

In particular, as shown by K. H. Jun, et al., "Simulation of depolarization effect by a rough surface for spectroscopic ellipsometry," J. Opt. Soc. Am. A, 20(6), 1060, (2003), which is incorporated by reference as if fully set forth herein, surface roughness is another important source of depolarization. In general, it is difficult to separate the surface plasmon induced depolarization from the depolarization caused by surface roughness and LER.

The embodiments described herein allow separation of both surface plasmon induced depolarization and depolarization caused by surface roughness and LER by using the advantageous attributes of AOI and azimuthal angle selectivity, as well as the capabilities of varying the angular extensions in both AOI and azimuthal angle directions (i.e., the NAs in both directions). Jun et al. show that the surface roughness induced depolarization strongly depends on the AOI. On the other hand, the surface plasmon induced depolarization depends on the NAs. The systems embodiments described herein allow the adjustment of both AOI and azimuthal angle, as well as the NAs in both directions. These capabilities, in addition to allowing these two root causes of depolarization to be separated, and hence further enhance the sensitivity, also enable measurement of LER by analyzing the relationship between LER induced depolarization and statistical variables of LER, such as root-mean-square and autocorrelation length of LER, which characterize LER and provide means for process control.

Another embodiment relates to a method for measuring one or more characteristics of patterned features on a specimen. The method includes acquiring measurements of light scattered from the patterned features on the specimen at multiple AOIs, multiple azimuthal angles, and multiple wavelengths simultaneously. The method also includes determining the one or more characteristics of the patterned features from the measurements. The one or more characteristics of the patterned features may include any of the characteristic(s) (e.g., CD) described herein.

In one embodiment, the method includes selecting the multiple AOIs and the multiple azimuthal angles such that the measurements of the light include measurements of SPWs. In another embodiment, the measurements of the light include measurements of SPWs and guided waves, and the one or more characteristics include CD of the patterned features. In such an embodiment, the measurements are more sensitive to the CD than if the measurements do not include the measurements of the SPWs and the guided waves. In an additional embodiment, the one or more characteristics include CD of the patterned features, and the multiple AOIs and the multiple azimuthal angles are selected such that the measurements are more sensitive to the CD than if the measurements were acquired at different AOIs and different azimuthal angles.

In some embodiments, the method includes selecting the multiple AOIs based on an optimal AOI and potential variations in the one or more characteristics. In one such embodiment, the method also includes selecting the multiple azimuthal angles based on an optimal azimuthal angle and the potential variations in the one or more characteristics.

In one embodiment, the method includes rotating the specimen such that the measurements can be acquired at the multiple AOIs and the multiple azimuthal angles.

In another embodiment, the method includes adjusting an exit aperture such that the measurements can be acquired at the multiple AOIs and the multiple azimuthal angles. In a further embodiment, the multiple AOIs and the multiple azimuthal angles are mapped across two dimensions of an exit aperture.

In one embodiment, the multiple wavelengths are mapped along a first dimension of a two-dimensional detector, and the multiple AOIs and the multiple azimuthal angles are mapped along a second dimension of the detector. In another embodiment, the multiple AOIs and the multiple azimuthal angles are mapped across two dimensions of an exit aperture, and the multiple AOIs and the multiple azimuthal angles are mapped along one dimension of the detector. In one such embodiment, the method includes directing light from the two dimensions of the exit aperture to the one dimension of the detector.

In some embodiments, the method includes electronically adjusting a two-dimensional detector such that the measurements can be acquired at the multiple AOIs and the multiple azimuthal angles. In another embodiment, the method includes averaging the measurements at the multiple AOIs and the multiple azimuthal angles over a portion of a NA of a collection system.

In one embodiment, the measurements of the light are responsive to surface plasmon induced depolarization of the light, and the one or more characteristics include CD and profile of the patterned features. In one such embodiment, the measurements are more sensitive to the CD and the profile than measurements that are not responsive to the surface plasmon induced depolarization. In another embodiment, the one or more characteristics include LER of the patterned features. In one such embodiment, the method includes determining the LER by determining surface plasmon induced depolarization of the light and LER induced depolarization of the light using the measurements at the multiple AOIs and the multiple azimuthal angles.

In some embodiments, the measurements include ellipsometric measurements. In another embodiment, the measurements include reflectometric measurements. In one embodiment, the method includes illuminating the specimen by directing the chief ray of illumination to the specimen at an oblique AOI. In a further embodiment, the patterned features include isolated patterned features.

Each of the steps of the various embodiments of the method described above may be performed as described further herein. In addition, each of the method embodiments described above may be performed by the system embodiments described herein. Furthermore, each of the method embodiments described above may include any other step(s) described herein. Moreover, each of the method embodiments described above has all of the advantages of other embodiments described herein.

Further modifications and alternative embodiments of various aspects of the invention may be apparent to those skilled in the art in view of this description. For example, systems and methods for measuring one or more characteristics of patterned features on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to measure one or more characteristics of patterned features on a specimen, comprising:
    an optical subsystem configured to acquire measurements of light scattered from the patterned features on the specimen at multiple angles of incidence, multiple azimuthal angles, and multiple wavelengths simultaneously; and
    a processor configured to determine the one or more characteristics of the patterned features from the measurements, wherein the measurements at the multiple angles of incidence and the multiple azimuthal angles are averaged over a portion of the numerical aperture of the optical subsystem.

2. The system of claim 1, wherein the one or more characteristics comprise critical dimension of the patterned features.

3. The system of claim 1, wherein the multiple angles of incidence and the multiple azimuthal angles are selected such that the measurements of the light comprise measurements of surface plasmon waves and guided waves.

4. The system of claim 1, wherein the measurements of the light comprise measurements of surface plasmon waves and guided waves, wherein the one or more characteristics comprise critical dimension of the patterned features, and wherein the measurements are more sensitive to the critical dimension than if the measurements do not comprise the measurements of the surface plasmon waves and the guided waves.

5. The system of claim 1, wherein the one or more characteristics comprise critical dimension of the patterned features, and wherein the multiple angles of incidence and the multiple azimuthal angles are selected such that the measurements are more sensitive to the critical dimension than if the measurements were acquired at different angles of incidence and different azimuthal angles.

6. The system of claim 1, wherein the multiple angles of incidence are selected based on an optimal angle of incidence and potential variations in the one or more characteristics, and wherein the multiple azimuthal angles are selected based on an optimal azimuthal angle and the potential variations in the one or more characteristics.

7. The system of claim 1, further comprising a stage configured to support the specimen during acquisition of the measurements, wherein the stage is further configured to rotate the specimen such that the measurements can be acquired at the multiple azimuthal angles.

8. The system of claim 1, wherein the optical subsystem comprises an exit aperture that is adjustable such that the measurements can be acquired at the multiple angles of incidence and the multiple azimuthal angles.

9. The system of claim 1, wherein the optical subsystem comprises an exit aperture, and wherein the multiple angles of incidence and the multiple azimuthal angles are mapped across two dimensions of the exit aperture.

10. The system of claim 1, wherein the optical subsystem comprises a two-dimensional detector, wherein the multiple wavelengths are mapped along a first dimension of the detector, and wherein the multiple angles of incidence and the multiple azimuthal angles are mapped along a second dimension of the detector.

11. The system of claim 1, wherein the optical subsystem comprises an exit aperture, a two-dimensional detector, and a set of optical fibers, wherein the multiple angles of incidence and the multiple azimuthal angles are mapped across two dimensions of the exit aperture, wherein the multiple angles of incidence and the multiple azimuthal angles are mapped along one dimension of the detector, and wherein the set of optical fibers is configured to direct light from the two dimensions of the exit aperture to the one dimension of the detector.

12. The system of claim 1, wherein the optical subsystem comprises a two-dimensional detector that is electronically adjustable such that the measurements can be acquired at the multiple angles of incidence and the multiple azimuthal angles.

13. The system of claim 1, wherein the measurements of the light are responsive to surface plasmon induced depolarization of the light, wherein the one or more characteristics comprise critical dimension and profile of the patterned features, and wherein the measurements are more sensitive to the critical dimension and the profile than measurements that are not responsive to the surface plasmon induced depolarization.

14. The system of claim 1, wherein the one or more characteristics comprise line edge roughness of the patterned features, and wherein the processor is further configured to determine the line edge roughness by determining surface plasmon induced depolarization of the light and line edge roughness induced depolarization of the light using the measurements at the multiple angles of incidence and the multiple azimuthal angles.

15. The system of claim 1, wherein the measurements comprise ellipsometric measurements.

16. The system of claim 1, wherein the measurements comprise reflectometric measurements.

17. The system of claim 1, wherein the optical subsystem is further configured to direct the chief ray of illumination to the specimen at an oblique angle of incidence.

18. The system of claim 1, wherein the patterned features comprise isolated patterned features.

19. A method for measuring one or more characteristics of patterned features on a specimen, comprising:
   acquiring measurements of light scattered from the patterned features on the specimen at multiple angles of incidence, multiple azimuthal angles, and multiple wavelengths simultaneously; and
   determining the one or more characteristics of the patterned features from the measurements, wherein the measurements at the multiple angles of incidence and the multiple azimuthal angles are averaged over a portion of a numerical aperture of an optical subsystem used to acquire the measurements.

20. A system configured to measure one or more characteristics of patterned features on a specimen, comprising:
   an optical subsystem configured to acquire measurements of light scattered from the patterned features on the specimen at multiple angles of incidence, multiple azimuthal angles, and multiple wavelengths simultaneously, wherein the optical subsystem comprises an exit aperture, a two-dimensional detector, and a set of optical fibers, wherein the multiple angles of incidence and the multiple azimuthal angles are mapped across two dimensions of the exit aperture, wherein the multiple angles of incidence and the multiple azimuthal angles are mapped along one dimension of the detector, and wherein the set of optical fibers is configured to direct light from the two dimensions of the exit aperture to the one dimension of the detector; and
   a processor configured to determine the one or more characteristics of the patterned features from the measurements.

* * * * *